United States Patent [19]

Spits

[11] Patent Number: 4,737,141

[45] Date of Patent: Apr. 12, 1988

[54] METHOD OF DRAINING THE MAXILLARY SINUS FOR THE TREATMENT OF MAXILLARY SINUSITIS

[75] Inventor: Marc Spits, Achel, Belgium

[73] Assignee: Fundatech S.A., Switzerland

[21] Appl. No.: 808,444

[22] Filed: Dec. 12, 1985

Related U.S. Application Data

[63] Continuation of Ser. No. 633,886, Jul. 24, 1984, abandoned.

[30] Foreign Application Priority Data

Jul. 26, 1983 [NL] Netherlands .......................... 8302648

[51] Int. Cl.⁴ ............................................. A61M 27/00
[52] U.S. Cl. ........................................ 604/28; 604/54;
604/106

[58] Field of Search ....................... 604/48, 49, 51, 54,
604/106, 158, 161, 264, 274, 280, 28

[56] References Cited

U.S. PATENT DOCUMENTS 3,592,197  7/1971  Cohen .............................. 604/280 X
3,804,097  4/1974  Rudie ..................................... 604/28
4,239,042 12/1980  Asai ....................................... 604/164

Primary Examiner—Stephen C. Pellegrino
Attorney, Agent, or Firm—Kane, Dalsimer, Sullivan, Kurucz, Levy, Eisele and Richard

[57] ABSTRACT

Maxillary sinusitis is treated by placing a self-supporting temporary drain hose in a wall separating the sinus and a nasal cavity. The hose allows drainage from the sinus, and repeated rinsings without the need of further operations. Between rinsings, air enters the sinus through the hose and kills bacteria therein.

9 Claims, 2 Drawing Sheets

METHOD OF DRAINING THE MAXILLARY SINUS FOR THE TREATMENT OF MAXILLARY SINUSITIS

RELATED APPLICATIONS

This is a continuation application to application Ser. No. 633,886, filed July 24, 1984 now abandoned.

BACKGROUND OF THE INVENTION

1. Field of Invention

This invention relates to a procedure or method of draining a patient's sinus maximus by creating a temporary passage to a nasal cavity.

2. Description of the Prior Art

The maxillary sinus is an air-filled space clad with mucous membrane and opening through a narrow discharge passage into the nose under the middle nose scoop. An inflammation of the maxillary sinus is accompanied by the generation of pus by an inflamed mucous membrane. Usually, pus discharge is possible from the maxillary sinus to the nose through the normal discharge passage. However, for a severe inflammation of the maxillary cavity, so much pus is produced that it cannot be discharged through the normal discharge opening, or alternatively the mucous membrane in the discharge passage is thickened by the inflammation thereby closing the discharge opening.

Maxillary sinusitis has been generally treated with repeated so-called classical antral lavages. These classical antral lavages are painful for the patient, and unpleasant and time-consuming for the doctor. The antral lavages are frequently followed by the administration of various drugs. If the condition becomes chronic, a Claue operation or a Caldwall-Luc operation is also performed.

The purpose of an antral lavage is the removal of pus from the maxillary sinus. In a classical antral lavage under a local anaesthetic the partition wall between nose and maxillary sinus is pierced under the lower nose scoop. This partition wall successively consists of nose mucous membrane, bone, and periosteum at both sides of the bone and mucous membrane in the maxillary sinus. The mucous membrane on the nose side is locally anaesthetized. However, the mucous membrane on the maxillary sinus side, the periosteum adjacent the bone and the bone itself are not anaesthetized. The partition wall between nose and maxillary sinus is pierced with an antral lavage needle. After the antral lavage needle has pierced the partition wall the maxillary sinus is rinsed with a rinsing fluid. After rinsing, the needle is retracted into the nose and thereafter removed. The hole made in the partition wall by the needle heals within a day. Within several days, pus may be produced again and the whole procedure must be repeated.

The classical antral lavages are continued until the maxillary sinus stops producing pus. Typically, a relatively large number of such operations are required before the condition is required, with five being about average.

These repeated classical antral lavages are rather time-consuming for patient and physician. For each classical antral lavage the nose must be locally anaesthetized as described above. The local anaesthesia takes effect in about fifteen minutes so that at least 20 minutes are required for each antral lavage.

The treatment of the maxillary sinusitis with classical antral lavages thus means for the patient at least on the average five, painful, unpleasant and time-consuming treatments and for the physician at least on the average five unpleasant and time-consuming treatments of the patient.

OBJECTIVES AND SUMMARY OF THE INVENTION

In view of the above, it is a principal objective of the present invention to provide a method of treating maxillary sinusitis which requires a single operation regardless of the length of time necessary for the sinus to heal.

A further objective is to provide (at least temporarily) a continuous passage which is unaffected by the inflamed sinus mucous membrane for draining the sinus and simultaneously to provide air into the sinus to eliminate the anaerobic bacteria which may cause the condition.

Yet another objective is to provide a method which allows the sinus to be rinsed as often as required, without any pain and discomfort to the patient.

Other objectives and advantages of the invention shall become apparent from the following description of the invention. In accordance with the present invention, maxillary sinusitis is treated by simultaneously cutting an opening in the maxillary sinus and nasal passage and installing therebetween a self-retaining hose. The hose provides a means by which pus drains automatically into the nose so that the patient may get rid of it by merely blowing his nose. Air also gets into the sinus to kill the anaerobic bacteria as mentioned above. Finally, the hose may be connected to a source of running fluid, if rinsing of the sinus is indicated.

DETAILED DESCRIPTION OF THE PREFERRED EMBODIMENT

Figure 1:
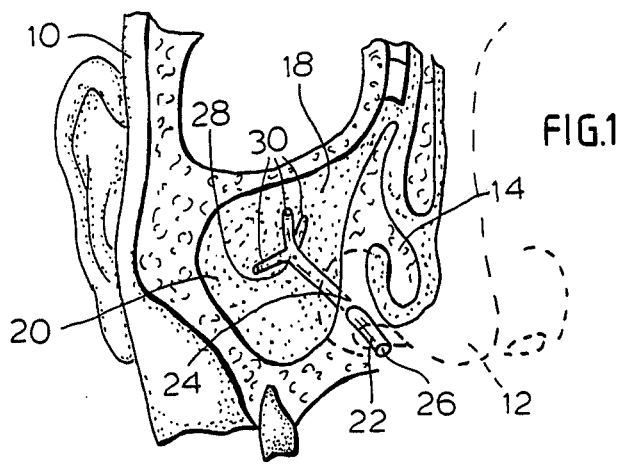
FIG. 1 discloses a sinus drain hose installed in accordance with the present procedure.

In FIG. 1, patient 10 has a nose 12 (shown in phantom lines) with a nasal passage 14, and a maxillary sinus 18 filled with pus 20. In order to drain the pus 20 from sinus 18, a drain hose 22 is installed between a wall 24 separating sinus 18 from passage 14. The drain hose is made of a plastic material and has an outer end 26 communicating with passage 14 and distal end 28 communicating with sinus 18. At distal end 28, the drain hose is formed with a plurality of projections 30 which extend away from the hose shown, so that the hose 22 is not dislodged easily from the wall 24.

Figure 2A:
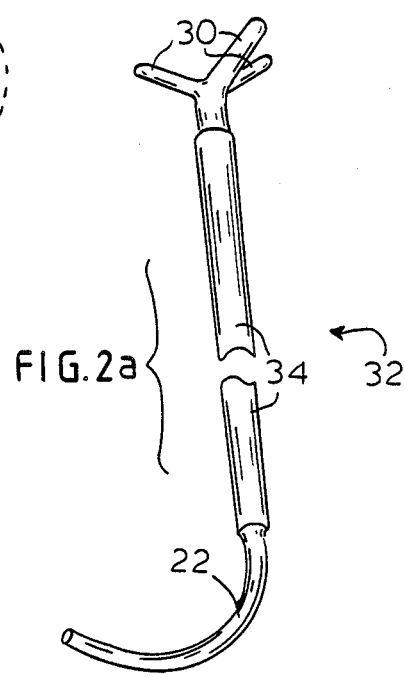
FIG. 2a shows details of the drain hose assembly prior to installation.

Prior to its installation, the drain hose is provided as part of a drain hose assembly shown in FIG. 2a. The drain hose assembly 32 comprises the drain hose 22

Figures 2B, 2C:
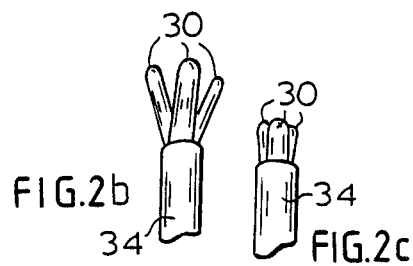
FIG. 2b shows the drain assembly of FIG. 2a with the projections partially collapsed.
FIG. 2c shows the drain assembly of FIGS. 2a and 2b with the projections completely collapsed.

(which is still several inches in length) and a hose sleeve 34 telescopically mounted on the hose. In the configuration of FIG. 2a the sleeve is pulled away from the distal hose end 26, and projections 30 are in a first position in which they are disposed radially outward from the hose 22. These projections are flexible so that as the sleeve is gradually pulled axially over them, they start collapsing radially inwardly (as shown in FIG. 2b) until a second position is reached (shown in FIG. 2c) in which they fit within the sleeve 34 approximately in parallel with the axis of the hose.

Figure 3:
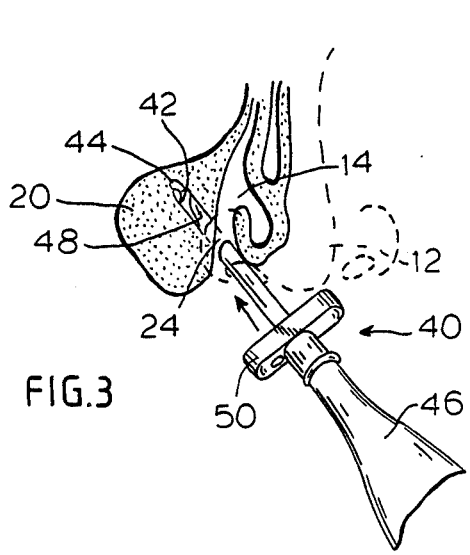
FIG. 3 shows the step of making an opening in the wall between the maxillary sinus and a nose passage.

The subject procedure is started by first anaesthesizing the nose 10 and introducing an antrcscopic trocar 40 partially into nose passage 14 for piercing wall 24 (FIG. 3). The trocar includes a needle 42 with a sharp tip 44 and a handle 46. A trocar sleeve 48 is telescopically disposed around the needle 42 and is terminated by an enlarged head 50 so that the needle and the sleeve can be manipulated independently.

Figure 4:
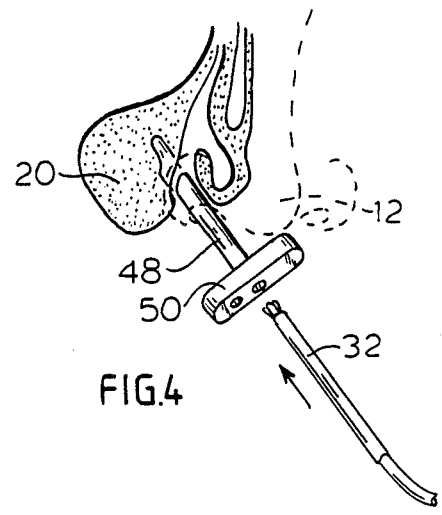
FIG. 4 shows the drain hose assenbly of FIG. 2a being installed.
Figure 5:
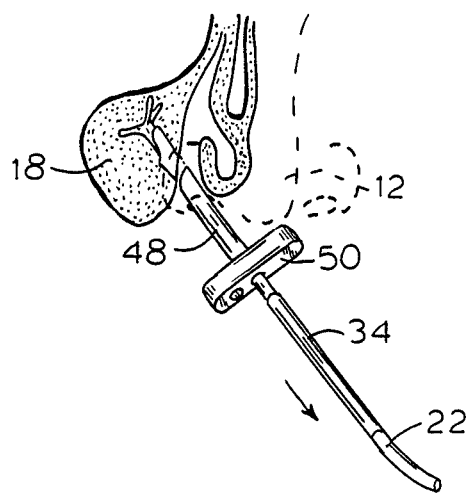
FIG. 5 shows the removal of the drain assembly sleeve.

After the wall 24 between sinus 18 and nasal passage 14 has been pierced, needle 42 is withdrawn leaving the trocar sleeve 48 in place as shown in FIG. 4. The distal end of the drain hose is then inserted through trocar sleeve 24 with the projections 30 in the second position within sinus cavity 18. The hose sleeve 34 is then removed from the hose 22 allowing projections 30 to separate (FIG. 5) and rotate toward the first position, i.e. at an angle with respect to a hose longitudinal axis. In this position the projections provide a means by which the hose is retained within the nose.

Figure 6:
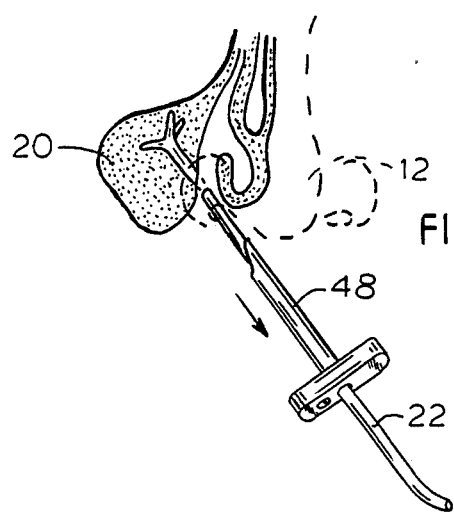
FIG. 6 shows the removal of the trocar sleeve.
Figure 7:
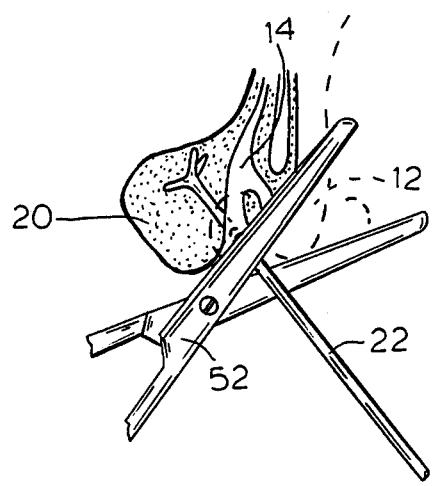
FIG. 7 shows the drain hose being cut to size.

Finally, the trocar sleeve 48 is also removed (FIG. 6) and the hose 22 is cut near the end of nasal passage 14 by scissor 52 (FIG. 7) thereby leaving the drain in the position shown in FIG. 1.

The insertion of the sinus drain maybe as painful as a classical antral lavage, but when the sinus drain is in situ, the maxillary sinus can be rinsed as often as necessary without the need of further operations. Alternately, the sinus may be rinsed at preset intervals. These washings are not painful for the patient, nor unpleasant or time-consuming for physician and patient.

Thus, the use of the sinus drain saves the patient and the physician many unpleasant, painful and time-consuming antral lavages. When the maxillary sinusitis is cured, which may be indicated by the lack of pus from the maxillary sinus, the hose can be easily removed from the maxillary sinus by pulling on the hose 22 thereby causing the projection 30 to fold together to form an extension of the flexible hose 22.

Obviously, numerous modifications may be made to the invention without departing from its scope as defined in the appended claims.

What is claimed is:

1. A method of treating maxillary sinusitis on a patient with a maxillary sinus comprising the steps of:
    making an opening in a wall of said maxillary sinus;
    placing a self-supporting hose within said opening for communicating with said sinus the hose having means at the distal end thereof to retain said hose within the sinus cavity;
    performing the steps of draining the sinus and rinsing the sinus through the hose at desired intervals.

2. The method of claim 1 wherein said sinus is rinsed at preset intervals.

3. The method of claim 1 wherein between rinsings, the hose is left open to allow air into the sinus for killing anaerobic bacteria therein.

4. The method of claim 1 further comprising removing the hose after the sinus has been cured.

5. A method of treating maxillary sinusitis of a patient comprising the steps of:
    providing a drain hose assembly with a drain hose having a distal end, and several projections attached to said distal end, said projections being flexibly movable between a first position in which the projections extend radially away from said hose and a second position in which the projections are substantially in parallel with a hose axis; and a hose sleeve telescopically mounted on said hose, said sleeve being axially movable on said hose for moving said projections between said first and second positions;
    making an opening in a wall between a maxillary sinus and a nasal opening;
    inserting the distal end of said drain hose assembly through said opening into said sinus with said hose sleeve positioned to keep said projection in said second position; and
    moving said sleeve axially to shift said projections to said first position for retaining the hose in the sinus.

6. The method of claim 5 further comprising removing said hose sleeve from said hose.

7. The method of claim 5 further comprising cutting said hose to a predetermined size.

8. The method of claim 5 wherein said opening is made by inserting a trocar through said wall.

9. The method of claim 7 where said trocar has a needle surrounded by a trocar sleeve said needle being withdrawn after the opening has been made, and said distal end being inserted into said sinus through said trocar sleeve after the withdrawal of the needle.

* * * * *